Figure 1:
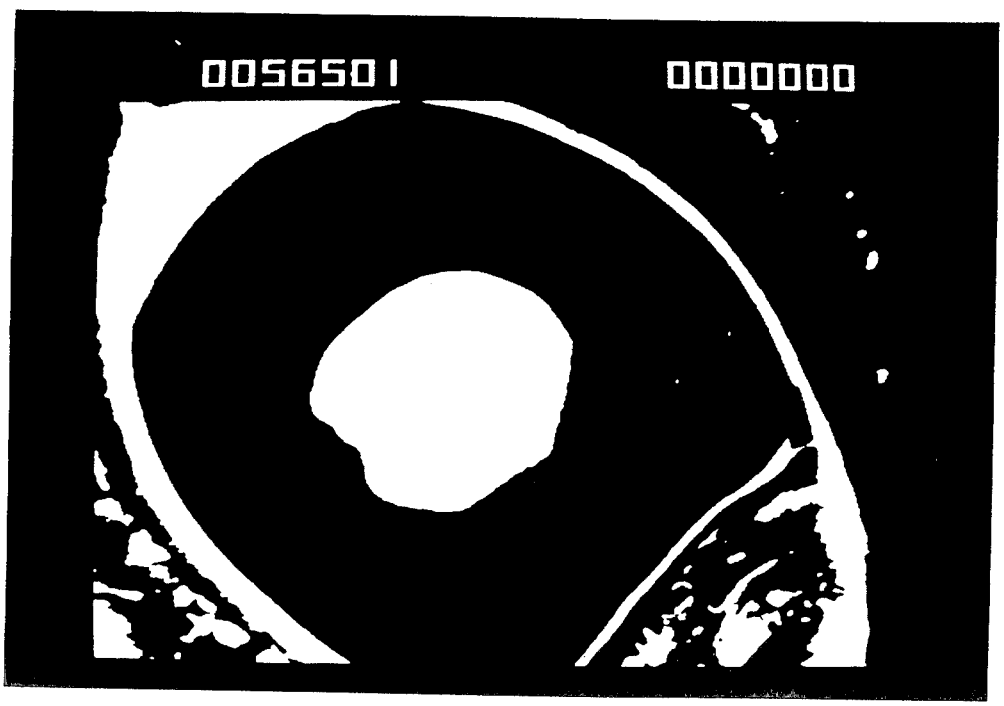

United States Patent [19]

Courtois et al.

[11] Patent Number: 4,477,435

[45] Date of Patent: Oct. 16, 1984

[54] METHOD FOR REGENERATING CORNEAL EPITHELIUM

[75] Inventors: Yves Courtois, Gif sur Yvette; Denis Barritault; Yves Pouliquen, both of Paris, all of France

[73] Assignee: Institut National de la Sante et de la Recherche Medicale (INSERM), Paris, France

[21] Appl. No.: 429,798

[22] Filed: Sep. 30, 1982

Related U.S. Application Data

[63] Continuation of Ser. No. 265,194, May 19, 1981, abandoned.

[51] Int. Cl.³ .............................................. A61K 35/12
[52] U.S. Cl. ....................................................... 424/95
[58] Field of Search ........................................ 424/95

[56] References Cited

PUBLICATIONS

Kishimoto et al., Acta. Soc. Ophthal. Japan, vol. 68, pp. 1145–1158.
Arruti et al., Experimental Cell Research, vol. 117 (1978), pp. 283–292.

*Primary Examiner*—Sam Rosen
*Attorney, Agent, or Firm*—Oblon, Fisher, Spivak, McClelland & Maier

[57] ABSTRACT

A composition and a method for regenerating wounded or damaged corneal epithelium are described. The composition comprises an aqueous solution containing an effective amount of ocular extract RE. The RE is extracted from eye tissues, such as choroid, iris and vitreous as well as aqueous humor. The active extract is obtained by the treatment of bovine ocular tissues with a buffered aqueous saline solution at pH of about 7.2. For ophthalmological use, the RE extract is purified by precipitation with acetic acid and dialyzed against physiologic saline NaCl solution. Such a composition is shown to increase significantly the rate of healing of wounded corneal epithelium.

4 Claims, 3 Drawing Figures

FIG_1

CONTROL
EDGF treated
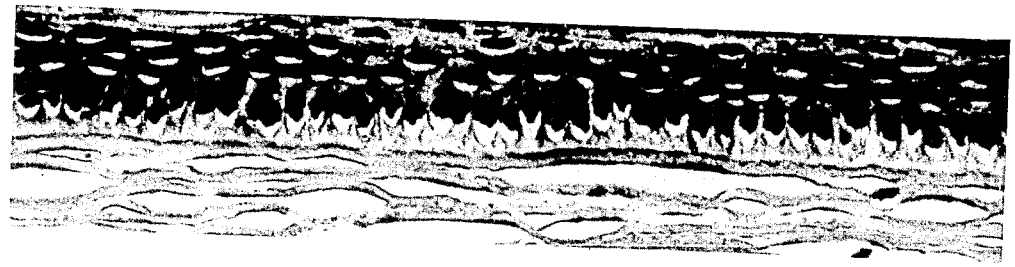
FIG_3

METHOD FOR REGENERATING CORNEAL EPITHELIUM

This is a continuation of application Ser. No. 265,194, filed May 19, 1981, now abandoned.

The invention relates to a composition and a method for healing eyes and more particularly for regenerating wounded or damaged corneal epithelium.

The co-pending international application No. PCT FR No. 80/00118 filed July 10, 1980 for "A process for stimulating the growth of human epidermal cells, application of said process and products applying the said process", relates to processes and products applicable to the human skin and more particularly to the adult human epidermis. Its object is notably a process for stimulating the growth of human epidermal cells, particularly those of adults, as well as cosmetic, pharmaceutical and diagnostic products using the said process.

The invention claimed in said co-pending application can be used, by way of example, in the treatment of burns, in the fields of cosmetics and of cutaneous pharmacology and for long-term culture of epidermal cells.

However, this prior application does not teach the treatment of eye cornea. The corneal tissue basically differs in its nature from the epidermal cells.

The present invention calls upon previous work reported by ARRUTI C. and COURTOIS Y. Exptl. Cell. Res. 117, 283–292 (1978). These authors established that a retinal extract, referred to by the abbreviation RE, was a growth-promoting factor for cultured epithelial lens cells. This article which is introduced in the present specification by way of reference describes retinal extract RE, and some properties of it. The authors used a total retinal extract obtained by extraction with an aqueous salt solution, with a pH 7.2 isotonic phosphate buffer known as PBS in the art. The bovine retinas are placed in intimate contact with such a solution. After a certain number of physical centrifugation and filtration techniques the retinal extract RE is isolated. However, the observations reported in this article are limited to the growth of epithelial lens cells.

Certain documents relating to the prior technique describe work on extracts obtained from animal ocular tissue.

French Pat. No. 71 13 756 (publication No. 2,134,088) describes a process for obtaining a total bovine eyeball extract. The series of steps involves the action of merthiolate, of an alkaloid and of "Celite".

The alcoholic extract so obtained is applied in the field of ophthalmology. It is not, therefore, an aqueous saline solution.

The article by B. S. Kasavina et al (Columbus, Ohio, USA) and SU Pat. No. 130.159 of the July 15, 1960 cited in Chemical Abstracts Vol. 55, no 5 (Mar. 6, 1961) no. 4892c describe the preparation of a product containing hyaluronic acid by extraction from the vitreous humor of cattle eyes, and its application to the treatment of infected wounds. The product is a chloroformic extract.

It is therefore clear that the prior technique does not teach a factor consisting of an aqueous extract of ocular tissue that is effective for regenerating corneal epithelium.

It would be emphasized that epithelial cells of the cornea are very different in their nature from the epithelial cells of crystalline lens and still more from epidermal cells, on which prior studies were effected. In a field as the one of the invention, it is impossible to the one skilled in the art to make serious anticipations, when he knows that the cells of a same organ, such as eye, are of different nature and do not reply in the same manner to a determined stimulus.

Many corneal conditions are associated with breaks in the epithelium: inflammation, infection, trauma, dystrophies and trophic problems. Although they have different pathogenic mechanisms, a primary consideration in the management of these conditions is the integrity of the epithelium. An unhealed epithelium increases jeopardy from proteolytic enzymes and infections. Once the epithelium has healed topical corticosteroid may be applied more safely in appropriate cases. It has been known for some time that stromal wounds require epithelium to heal.

According to one aspect of the invention, it is provided a method for regenerating wounded or damaged corneal epithelium comprising the step of contacting said epithelium with an aqueous salt extract of ocular tissue (RE extract).

According to another aspect of the invention, it is provided a composition for regenerating wounded or damaged corneal epithelium, comprising an aqueous solution containing an effective amount of ocular extract RE.

To obtain the active RE agent, the technique described in the above mentioned article by C. ARRUITI and Y. COURTOIS can be used. The starting material, namely bovine retinas, is easily available and abundant.

The expression "ocular tissue extract" designates a product that can be extracted from various tissues of the eye, such as choroid, iris and vitreous as well as aqueous humor. It does not include the crystallin lens.

To effect extraction, any aqueous salt solution is used, buffered to a pH of approximately 7.2 and capable of providing an aqueous extract containing the RE. For ophthalmological use, according to the present invention, the extract was partially purified by precipitation with 0.1N acetic acid and dialysed against physiologic saline NaCl solution.

Various concentrations of the RE factor can be used in the composition according to the invention. The man skilled in the art is able to select the appropriate concentration to be used depending upon the severity of the corneal epithelial injury and the duration of the treatment. Of course, local application can be repeated to provide the necessary amount of active agent. For example, compositions containing 1 mg and 10 $\mu$g of RE factor per ml were equally effective in the long term to accelerate the complete epithelium reorganization.

Numerous practical experiments were carried out with RE concentration in 0.1N solution equal respectively to 0.01 mg/ml; 0.1 mg/ml and 1 mg/ml.

At the lowest concentration 0.01 mg/ml, a significant effect was observed after a long-term treatment (6 days) in respect of the cicatrization quality (Table II).

At the intermediate dosage 0.1 mg/ml, a significant acceleration of the cicatrization speed was further observed.

At the maximal dosage 1 mg/ml, the acceleration of the cicatrization speed is maximal.

It should be noted that the concentration in RE factor to be used in each case also depends on the frequency of the eye treatment. Ordinarily, the treatment process according to the invention involves the repeated contact of the damaged eye cornea with the active solution containing RE. In the practical tests, which were carried out, a drop, i.e. 50 μg of RE solution 0.1N was used in each eye every four hours.

Different application frequencies may also be used in order to take into account the severity of the damages to be treated. With treatment frequencies in the range of one drop per eye every four hours, the range of RE concentration is preferably between about 0.01 an 1 mg/ml.

With such concentrations, the frequency of application is advantageously at least three times per day.

In vivo studies have shown that the composition according to the invention is able to increase significantly the rate of healing of rabbit corneal epithelium wounded by iodine vapors. Conversely, other commercially available healing substances had no effect in comparable circumstances.

It has also been established that the RE factor used according to the invention is not toxic.

The invention will now be illustrated in greater detail, while in no way being limited thereto, by experiments on rabbit eyes.

The purpose of the following disclosure is to report the effect of EDGF on the rate of epithelial healing in vivo and to compare it with putative effects of commercially available healing substances.

Several techniques have been used to determine the rate of epithelium healing. We used a method of iodine vapor cautery described by Moses, Parkinson and Schuchart, 1979 [A standard large wound of the corneal epithelium in the rabbit. Invest. Ophthalmol.18, 103–106] Recordings of the lesions were measured by an image analyser. Recently Cintron, Hassinger, Kublan and Friend, 1979 [A simple method for the removal of rabbit corneal epithelium utilizing n-Heptanol. Ophthalmic Res.11 90–96.] demonstrated that both scraping and heptanol techniques to remove the epithelium destroy keratocytes which underlie the basement membrane. We have done transmission electron microscopy to study this possibility with our procedure. Histological studies have been performed to evaluate the quality of the regenerated epithelium.

RE factor was prepared according to the procedure described by Arruti and Courtois (cited supra). The extract was partially purified by precipitation with 0.1N acetic acid and dialysed against physiologic saline NaCl solution.

The solution contained 1 mg of protein ml$^{-1}$ and was used either pure or 100 times diluted.

As commercially available healing substances we used the following products.

"Vitacic" (Laboratoires H. Faure, France): a solution consisting of a mixture of adenosine,thymidine, cytidine,uridine,disodic GMP 5',Mercurothlolate and EDTA as preservatives.

"Keratyl" (Chauvin-Blache, France) consisting of nandrolone monosodic sulfate 1% and parahydroxybenzoate as preservative.

"Troformone" (Laboratoires Roussel, France) consisting of pancreatic extract.

A preservative consisting of a buffered solution of Na mercurothiolate 0.004% was also tested.

Pigmented rabbits of both sexes weighting 2 to 3 kilograms each were used in this study. Seventy eyes were divided into seven groups of ten eyes. At the completion of wound production described below, the eyes were treated according to the following protocol:

Group A receiving an isotonic NaCl solution, Group B mercurothiolate solution, Group C a mixture of nucleosides and nucleotides (Vitacic), Group D nandrolone, Group E pancreatic extract, Group F RE factor 0.02 mg ml$^{-1}$ and Group G RE factor 1 mg ml$^{-1}$. The substances were given four times a day.

After six days of treatment, four or five eyes from each group were enucleated, stained with hematoxylin and eosin and prepared for histologic examination.

The removal of rabbit corneal epithelium was performed in a similar manner to the method described by Moses, Parkinson and Schuchart (see supra). Iodine crystals were held in a glass tube by a plug of glass wool. Our tubes had an internal diameter of 7.3 mm at the tip.

The rabbits were anaesthetized with pentobarbital 30 mg/kg intraveneously. One drop of Novesine (oxybuprocaine hydrochlorate 0.4%) was installed in the eye and the eye was proplosed. The mouth of the tube was held against the cornea for a period of 3.5 min. Recording of the lesions was made by photography. The cornea was stained with 1 drop of 0.5% fluorescein (without preservatives) and flushed with 2 drops of isotonic NaCl solution. The lesions were photographed four times a day on Kodak Tri-X Pan film. An annular electronic flash covered with a Wratten 47 B filter was fixed around the objective of a slit lamp, the objective was covered with a Wratten 12 filter.

The negatives were processed by the T.V. scanner of the quantimet 720 of Cambridge Instruments U.K. and the area of the wound for each picture was measured and converted in square millimeters. FIG. 1 shows an example of a wound within the circular measurement frame as shown on the T.V. scanner screen. This frame defines the area within which measurements are made. Numbers at the top of the screen gives the area of the wound measured in picture points (pixels), before the millimeters connexion.

In a separate experiment we tested for iodine vapor damages to the basement membrane and keratocytes on two rabbit eyes. We used the same technique as described above to remove the epithelium. After 16 hours the rabbits were/sacrified, corneas were excised and stored in a 2.5% glutaraldehyde solution for two hours, washed in buffer, dehydrated in graded alcohol, embedded in a Araldite-Epon mixture. Ultra thin sections on a LKB ultramicrotome were obtained, stained with uranyl acetate and lead citrate, examined with a Philips EM 300 transmission electron microscope.

RESULTS

We tested the reproducability of our measurement system by taking five consecutive photographs of the same lesion. The measures obtained by the quantimet were homogenous at 1%.

Figure 2:
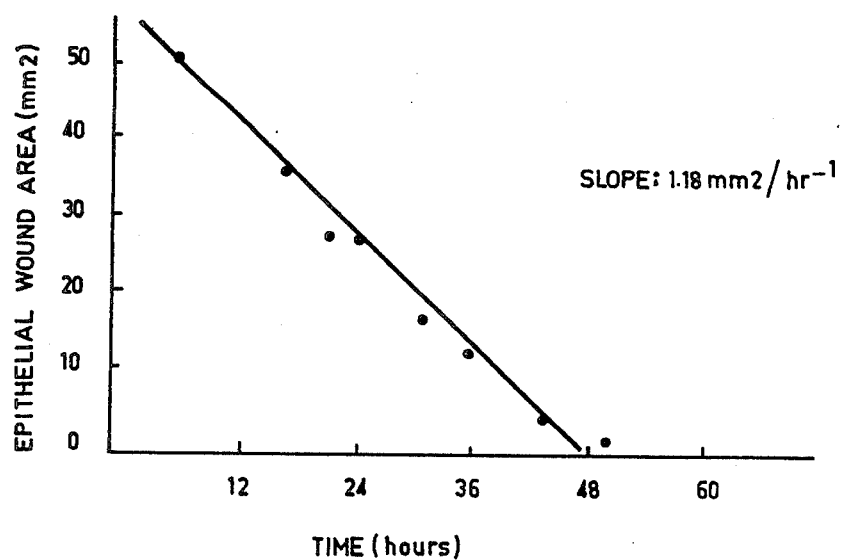

The mean diameter of central corneal wounds at 4 hours for each group ranged from 7.54 to 7.76 mm. P values obtained from Student t-test showed that the difference was not statistically significant at the 0.05 level. The wound area against the time were plotted and a healing curve for each eye was obtained. The best fitting curve by the least square method was obtained with a linear regression. FIG. 2 shows an example of healing curve of a control cornea.

All 68 slopes or healing rates computed by the linear regression method are listed in table I. The mean rates of epithelium healing were calculated for each of the 7 groups of animals. P-values obtained from Student t-tests indicated that the difference in the mean healing rates between the control group and the other groups was statistically insignificant at the 0.05 level except for RE 1 mg/ml treated group which was statistically significant at the 0.001 level. (See Table I hereinbelow).

Histologic examination of eyes enucleated after six days of treatment from Group A, C,D and E showed an epithelium composed of 3 to 5 layers in thickness. Most of the time the basal cells had a round shape and a round nucleus centrally positioned. RE treated groups (F and G) had four to six layers in thickness. The basal cells were more tightly packed, tall, polygonal and regular, in shape. The oval nucleus was oriented at a right angle to the surface of the cornea, and displaced towards the apex of the cell. Using an ocular micrometer grid fixed on the microscope we counted the number of basal cells on a 270 μm length unit. Nine measures were taken on three different sectors of the same cornea in a central zone of 5 mm radius. The table II summarizes the mean number of basal cells plus or minus variance per 270 μm on histological preparation. Four or five corneas were randomly chosen for each group. A one way analysis of variance indicated a statistically significant difference between control and RE 0.01 mg ml$^{-1}$ at 0.05 level and between control and RE 1 mg.ml$^{-1}$ at 0.01 level.

TEM micrographs of cornea 16 hours after removal of epithelium showed consistantly a naked basal lamina of normal appearance. The collagen and interfibrillar matrix showed no apparent changes. The cell membrane of the keratocytes beneath the denuded area was well defined, the intracellular organels, golgi apparatus and mitochondries were preserved. The nucleus had a normally distributed chromatin and a fibrillar matrix was visible probably due to a slight oedema.

In the drawings, FIG. 1 is a picture of epithelial wound as shown on the screen of the quantimet 720 Scanner. The central clear area corresponds to the surface of the wound and is enclosed in a black circle area representing the zone within which measurements are made. The number on the top represents the area of the wound in picture points.

FIG. 2 is a representative healing curve of rabbit cornea epithelium.

FIG. 3 comprises histological cross sections of healed epithelium after 6 days of treatment. Top(control) bottom (RE):note the differences in total thickness, in cell density, and in the regularity of the basal layer.

The various hereinbefore described data show that the only substance which displays a high significative activity on the rate of healing was RE at the highest concentration. All the other substances had statistically no effects on the rate of epithelial healing. Diluted RE did not increase this rate but significantly had a favorable effect on the organization of the epithelial layer after 6 days of treatment. The optimal concentration for RE in the eye was 1 mg ml$^{-1}$, or 200 times more concentrated that the effective solution in vitro. One very interesting point is the fact that RE is an eye derived growth factor. We have documented the fact that the same growth factor activity is present in the vitreous and in the retina. RE may have a physiological role in the normal eye but also in pathological conditions. Possibly its concentration varies as a function of age.

TABLE I

RATE OF DECREASE IN AREA OF EPITHELIAL WOUND (mm$^2$/hr.)

| Group A Control | Group B Mercurothiolate | Group C Nucleoside-Nucleotide | Group D Nandrolone | Group E Pancreatic extract | Group F RE 0.01 mg/ml | Group G RE 1 mg/ml |
|---|---|---|---|---|---|---|
| 1.16 | 1.11 | 1.42 | 1.22 | 1.12 | 1.26 | 1.53 |
| 1.19 | 1.29 | 1.11 | 1.13 | 1.18 | 1.30 | 1.45 |
| 1.17 | 1.25 | 1.39 | 1.09 | 1.21 | 1.02 | 1.40 |
| 1.19 | 1.16 | 1.19 | 1.26 | 1.40 | 1.10 | 1.20 |
| 1.08 | 1.04 | 1.02 | 1.21 | 1.55 | 1.21 | 1.32 |
| 1.17 | 1.05 | 1.08 | 1.17 | 1.00 | 1.28 | 1.70 |
| 1.23 | 1.10 | 1.22 | 1.03 | 1.20 | 1.12 | 1.23 |
| 1.14 | 1.31 | 1.13 | 1.18 | 1.35 | 1.12 | 1.57 |
| 1.12 | 1.20 | 1.50 | 0.99 | 1.02 | 1.25 | 1.61 |
| 1.23 | | 1.27 | | 1.34 | 1.24 | 1.53 |
| a. | | | | | | |
| 1.16 ± 0.05 | 1.17 ± 0.1 | 1.23 ± 0.16 | 1.14 ± 0.09 | 1.24 ± 0.17 | 1.19 ± 0.09 | 1.45 ± 0.16 |
| — | p > 0.05 | >0.05 | >0.05 | >0.05 | >0.05 | <0.001 |
| b. | | | | | | |
| 7.76 ± 0.29 | 7.63 ± 0.36 | 7.65 ± 0.56 | 7.66 ± 0.26 | 7.54 ± 0.14 | 7.71 ± 0.21 | 7.66 ± 0.29 |

Each value listed represents the healing rate obtained from an animal.
a. Mean healing rate ± standard deviation.
b. Mean diameter mm) at 4 hr ± standard deviation.

TABLE II

MEAN NUMBER OF BASAL CELLS ± PER 270 μm ON HISTOLOGICAL PREPARATION

| Group A Control | Group C Nucleoside-Nucleotide | Group D Nandrolone | Group E Pancreatic extract | Group F RE 0.01 mg/ml | Group G RE 1 mg/ml |
|---|---|---|---|---|---|
| 27.84 ± 11.50 | 29.13 ± 13.39 | 27.64 ± 10.87 | 26.60 ± 14.65 | 34.22 ± 11.03 | 35.28 ± 6.66 |
| (5) | (5) | (4) | (5) | (4) | (4) |
| — | p > 0.05 | >0.05 | >0.05 | <0.05 | <0.01 |

( ) Sample size

We claim:

1. A method for regenerating wounded or damaged corneal epithelium, comprising the step of: contacting said epithelium in vivo with a therapeutically effective amount of an aqueous salt extract of ocular tissue.

2. The method of claim 1, wherein said extract is obtained by extracting an eye tissue selected from the group consisting of retinal tissue, choroid tissue, iris tissue, vitreous humor and aqueous humor with an aqueous salt solution.

3. The method of claim 1, wherein said extract is obtained by extracting bovine ocular tissues with a buffered aqueous saline solution having a pH of about 7.2, purifying said extract by treatment with acetic acid, and dialyzing said treated extract against a physiologic saline NaCl solution.

4. The method of claim 1 or 3, wherein the amount of said extract applied ranges from 10 µg/ml to about 1 mg/ml.

* * * * *